(12) United States Patent
Sudhoff et al.

(10) Patent No.: US 12,187,669 B2
(45) Date of Patent: Jan. 7, 2025

(54) METHOD FOR PRODUCING METHIONINE (71) Applicant: EVONIK OPERATIONS GMBH, Essen (DE)

(72) Inventors: Daniel Sudhoff, Bergkamen (DE); Judith Hierold, Hanau (DE); Philipp Roth, Hanau (DE); Imad Moussallem, Hanau (DE); Ulf Bindernagel, Cologne (DE); Christian Renner, Gründau (DE)

(73) Assignee: Evonik Operations GmbH, Essen (DE)

( * ) Notice: Subject to any disclaimer, the term of this patent is extended or adjusted under 35 U.S.C. 154(b) by 697 days.

(21) Appl. No.: 17/413,540

(22) PCT Filed: Dec. 13, 2019

(86) PCT No.: PCT/EP2019/085005
§ 371 (c)(1),
(2) Date: Jun. 12, 2021

(87) PCT Pub. No.: WO2020/120720
PCT Pub. Date: Jun. 18, 2020

(65) Prior Publication Data
US 2022/0048855 A1    Feb. 17, 2022

(30) Foreign Application Priority Data
Dec. 14, 2018 (EP) ..................... 18212499

(51) Int. Cl.
*C07C 319/20*    (2006.01)
*C07D 233/76*    (2006.01)

(52) U.S. Cl.
CPC .......... *C07C 319/20* (2013.01); *C07D 233/76* (2013.01)

(58) Field of Classification Search
None
See application file for complete search history.

(56) References Cited

U.S. PATENT DOCUMENTS 2,797,148 A    6/1957    Carlson
2,899,274 A    8/1959    Smith et al.
(Continued)

FOREIGN PATENT DOCUMENTS

CA    1008847    4/1977
GB    936664    9/1963
(Continued)

OTHER PUBLICATIONS

International Search Report for corresponding international application PCT/EP2019/085005, filed Dec. 13, 2019.
Written Opinion of the International Searching Authority for corresponding international application PCT/EP2019/085005, filed Dec. 13, 2019.
(Continued)

*Primary Examiner* — Amy C Bonaparte
(74) *Attorney, Agent, or Firm* — Law Office of Michael A. Sanzo, LLC (57) ABSTRACT

The present invention pertains to a method for producing methionine or salts or derivatives thereof from hydrogen cyanide (HCN), the method comprising a step of producing 2-hydroxy-4-(methylthio)butyronitrile (MMP-CN), or a crude product mixture comprising MMP-CN, by contacting a hydrogen cyanide (HCN) process gas mixture prepared according to the Andrussow process from methane, ammonia and oxygen, with 3-methylmercaptopropionaldehyde (MMP), wherein the HCN process gas mixture is obtained from the crude HCN process gas mixture by adjusting the amount of ammonia to between 20% (v/v) and 60% (v/v) of the amount of the ammonia in the crude HCN process gas mixture.

9 Claims, 3 Drawing Sheets

(56) References Cited

U.S. PATENT DOCUMENTS

| | | | |
|---|---|---|---|
| 2,987,382 | A | 6/1961 | Endter et al. |
| 5,770,769 | A | 7/1998 | Geiger et al. |
| 8,546,601 | B2 | 10/2013 | Buss et al. |
| 9,206,121 | B2 | 12/2015 | Buss et al. |
| 10,899,706 | B2 * | 1/2021 | Hierold ................. C07C 323/58 |
| 2011/0171101 | A1 | 7/2011 | Schaefer et al. |
| 2011/0295006 | A1 | 12/2011 | Kobler et al. |

FOREIGN PATENT DOCUMENTS

| | | | |
|---|---|---|---|
| GB | 1108926 | | 4/1968 |
| JP | 2003-104959 | | 4/2003 |
| JP | 2003-104960 | | 4/2003 |
| WO | WO-2018114640 A1 * | 6/2018 | ........... C01C 3/0212 |

OTHER PUBLICATIONS

International Preliminary Report on Patentability for corresponding international application PCT/EP2019/085005, filed Dec. 13, 2019.
European Search Report and Search Opinion for corresponding European application EP 18212499, filed Dec. 14, 2018.
Asaro, "Hydrogen Cyanide by the Andrussow and BMA Processes," *PEP Review* Jul. 2015, pp. 1-48 (Oct. 2015).
Bruttel, et al., "Wasserbestimmung durch Karl-Fischer-Titration," printed in Switzerland by Metrohm Ltd., pp. 1-84, (2006).
Bruttel, et al., "Water Determination by Karl Fischer Titration," pp. 1-82, English language translation, 2006.
Ulmann's Encyclopedia of Industrial Chemistry; Gail, et al., (Cyano Compounds, Inorganic, pp. 673-710 (2012); published online Oct. 15, 2011, DOI: 10.1002/14356007.a08_159pub3.

* cited by examiner

METHOD FOR PRODUCING METHIONINE

FIELD OF THE INVENTION

The present invention relates to a method for producing 2-hydroxy-4-(methylthio)butyronitrile (MMP-CN) from 3-(methylthio)propanal (=methylmercaptopropionaldehyde, MMP) and ammonia-containing hydrogen cyanide (hydrocyanic acid, HCN); and to a process for producing methionine from the thus-obtained MMP-CN.

BACKGROUND OF THE INVENTION

2-Hydroxy-4-(methylthio)butyronitrile (MMP-CN) is an intermediate in the preparation of methionine and methionine derivatives, such as methionine hydroxyl analogue (MHA) and methionylmethionine (Met-Met).

Methionine is an essential amino acid which is used, inter alia, as supplement in feed.

In many common methods, methionine is produced as a racemate, a mixture of the D- and L-enantiomers, in a multi-stage chemical route, for example via the so-called hydantoin route from acrolein, methyl mercaptan, hydrogen cyanide and ammonia and carbon dioxide.

The second step, the synthesis of 5-(2-methylmercaptoethyl)hydantoin (hydantoin), can be carried out directly from MMP, HCN, ammonia and CO₂ or alternatively in two stages via the formation of the cyanohydrin precursor MMP-CN:

EP 0780370 A2 discloses a method for preparing methionine, in which MMP, HCN, ammonia and carbon dioxide react to give a methionine precursor, hydantoin (direct synthesis of hydantoin). The molar ratio of ammonia to MMP may be between 1.2 and 6 in this case and the molar ratio of ammonia to carbon dioxide is 1.2 to 4.0. According to this method, MMP is converted to the hydantoin in practically quantitative yield. The hydantoin thus prepared is then further cleaved to form a methionine salt. The ammonia and carbon dioxide formed by the cleavage may be recycled into the process.

JP 2003104959 A and JP 2003104960 A describe a similar method for reacting MMP with HCN, NH₃ and CO₂ to give hydantoin. Here, the molar ratios of ammonia to MMP and CO₂ to MMP can have values in each case from 1.5 to 2.5.

The earlier applications GB 936664 A and GB 1108926 A also describe a method for reacting MMP with HCN, NH₃ and CO₂ to give hydantoin by reacting aldehydes or ketones with an equimolar or excess amount of CO₂ and an excess of ammonia in aqueous milieu.

WO2012/113664 A1 and WO 2012/113665 A1 describe a method for preparing MMP-CN from MMP and HCN, the first step of the two-stage route to hydantoin mentioned above.

For producing the hydrocyanic acid (HCN) starting material, the most frequently used processes in industrial practice are the Andrussow process (DE 102007034715A1 and Chemie-Ing.-Techn., 1953, No. 12, pp. 697-701) and the BMA process (Blausäure [hydrocyanic acid] from Methane and Ammonia, DE1041476 and Chemie-Ing.-Techn., 1958, No. 5, pp. 305-310 [1]). Whereas in the reducing BMA process methane and ammonia are converted to hydrocyanic acid, the oxidizing Andrussow process proceeds from methane, ammonia and oxygen. Both methods are described in more detail in "Handbook of Heterogeneous Catalysis", editor: G. Ertl. et al, second edition, Vol. 5, Chapter 12.3 "Hydrocyanic Acid (HCN) Production" 2592-2609 [2] and in Ullmann's Encyclopedia of Industrial Chemistry, "Cyano Compounds, Inorganic" published online on 15 Oct. 2011, DOI: 10.1002/14356007.a08_159. pub3 [3].

Both the Andrussow and the BMA process proceed with incomplete conversion based on ammonia. The HCN crude gas stream leaving the reactor therefore comprises proportions of ammonia in both cases. Table 1 summarizes the typical contents of HCN and ammonia (in % by volume) for this gaseous product mixture directly after the HCN reaction

TABLE 1

| Process | HCN (vol %) | NH₃ (vol %) | NH₃/HCN (mol/mol) | Reference |
| --- | --- | --- | --- | --- |
| Andrussow | 7.0 | 1.7 | 0.24 | [2] |
| Andrussow | 7.6 | 2.3 | 0.30 | [3] |
| Andrussow | 6.6 | 2.6 | 0.39 | [1] |
| BMA | 22.9 | 2.5 | 0.11 | [3] |

The molar ratio NH$_3$/HCN (mol/mol) presented in Table 1 arises due to Avogadro's Law from the corresponding concentrations of ammonia and hydrocyanic acid in % by volume:

NH$_3$/HCN (mol/mol)=[NH$_3$ (vol %) in the product mixture]/[HCN (vol %) in the product mixture]

The gaseous product mixture directly after the HCN synthesis according to the Andrussow process comprises, in addition to HCN and ammonia, especially water but also methane, nitrogen, hydrogen, CO and CO$_2$ and other constituents. A typical composition of an HCN crude gas stream prepared according to the Andrussow process is: HCN: 7.6% by volume, NH$_3$: 2.3% by volume and H$_2$O: 23.1% by volume [3]. Typical yields in the formation of hydrocyanic acid, based on ammonia, are around 63%.

The crude HCN gas mixture is typically at temperatures of over 1000° C. directly after the preparation by the Andrussow process and is immediately cooled. The ammonia present in the crude HCN gas stream is immediately removed in all common processes, for example by washing with dilute sulfuric acid. Thereby, ammonium sulfate is formed.

Removal of ammonia is generally considered necessary to avoid autocatalytic exothermic hydrocyanic acid polymerization which occurs particularly at elevated pH and at phase transitions such as in the liquefaction of HCN.

According to Chemie-Ing.-Techn., 1953, No. 12, pp. 697-701, around 60% of the ammonia used is converted to hydrocyanic acid in the Andrussow process, 10% is lost via the offgas and 30% is bound as ammonium sulfate in the acid wash with sulfuric acid.

As shown above, the Andrussow HCN process traditionally results in a compulsory load of ammonium sulfate which has to be processed, logistically handled and marketed. For the production of methionine, the amount of ammonium sulfate from the HCN production typically totals 50 to 200 kg of ammonium sulfate per ton of methionine.

The problem of the unavoidable ammonium sulfate formation and the loss of used NH$_3$ has, for example, been addressed in the recently published patent application WO 2018/114640 A1. Said patent application provides an approach to an ammonium sulfate-free synthesis of 2-hydroxy-4-(methylthio)butyronitrile (MMP-CN) from MMP and gaseous hydrocyanic acid that has not been freed from ammonia. In this process, the crude HCN process gas is directly passed from the HCN reactor into the MMP-CN reactive absorber, where the crude HCN gas is reacted with MMP to form MMP-CN. In this process, the ammonia is chemically bound in form of the amino derivatives 2-amino-4-(methylthio)butyronitrile (MMP-AN) and 2,2'-bis(2-(methylmercaptoethyl)iminodiacetonitrile (iminodinitrile), both of which can later be converted to 5-(2-methylmercaptoethyl)hydantoin, an intermediate of the methionine synthesis.

However, the omission of the ammonia scrubbing step as proposed by WO 2018/114640 A1 at the same time eliminates the reduction of water content prior to MMP-CN synthesis, leading to a biphasic mixture in the storage tanks and/or in the reactive absorber. In this case, the volume ratio of the aqueous layer to the organic MMP-CN layer (which is denser) is between 1:2 and 1:6.

Since the aqueous layer still contains organic material, i.e. product, it cannot simply be removed and discarded. Its disposal, on the one hand, leads to loss of raw material and higher production costs and, on the other hand, requires high efforts in biological waste water treatment. The reprocessing of the aqueous layer requires complex processes and apparatuses/equipment.

In view of the above, it was a remaining need to provide new processes or methods for producing 2-hydroxy-4-(methylthio)butyronitrile (MMP-CN) in which, on the one hand, the amount of ammonium sulfate obtained as a by-product is significantly reduced vis-à-vis conventional MMP-CN processes applying ammonia scrubbing; and in which, on the other hand, biphasic mixtures as occurring in ammonium sulfate-free MMP-CN processes can be avoided.

Further, and particularly in view of economic requirements, a process for preparing MMP-CN providing flexibility with regard to the ammonium sulfate formation per ton of methionine was particularly desirable.

SUMMARY OF THE INVENTION

The present invention pertains to a method for producing 2-hydroxy-4-(methylthio)butyronitrile (MMP-CN), the method comprising contacting a hydrogen cyanide (HCN) process gas mixture prepared according to the Andrussow process from methane, ammonia and oxygen, with 3-methylmercaptopropionaldehyde (MMP), the method being characterized in that the HCN process gas mixture is obtained from the crude HCN process gas mixture by adjusting the amount of ammonia to between 20% (v/v) and 60% (v/v) of the amount of the ammonia in the crude HCN process gas mixture.

BRIEF DESCRIPTION OF THE FIGURES

REFERENCE NUMBERS/LETTERS AND EXPLANATIONS

A Andrussow HCN reactor
B ammonia scrubber
HCN stripper
D reactive absorber
(1) methane feed stream
(2) ammonia feed stream
(3) crude Andrussow HCN gas stream
(4) bypass stream
(5) crude ammonium sulfate stream
(6) stripped HCN recycle stream
(7) ammonium sulfate product mixture
(8) sulfuric acid feed stream
(9) ammonia-adjusted HCN gas stream
(10) MMP feed stream
(11) Offgas
(12) MMP-CN product mixture
(air) air feed stream The ammonia adjustment unit is marked in dotted lines.

DETAILED DESCRIPTION OF THE INVENTION

The present inventors have unexpectedly found a new method for producing 2-hydroxy-4-(methylthio)butyronitrile (MMP-CN) that provides flexibility in adjusting the ammonium sulfate production in the MMP-CN process, whereby the aforementioned problems of state-of-the-art-processes, such as the formation of biphasic mixtures in storage tanks and/or reactive absorbers can be avoided.

Accordingly, the present invention provides a method for producing 2-hydroxy-4-(methylthio)butyronitrile (MMP-CN), the method comprising contacting a hydrogen cyanide (HCN) process gas mixture prepared according to the Andrussow process from methane, ammonia and oxygen, with 3-methylmercaptopropionaldehyde (MMP), the method being characterized in that the HCN process gas mixture is obtained from the crude HCN process gas mixture by adjusting the amount of ammonia to between 20% (v/v) and 60% (v/v) of the amount of the ammonia in the crude HCN process gas mixture.

As used in the context of the present invention, the term "crude HCN process gas mixture" is to be understood as a HCN gas mixture as obtained from Andrussow HCN synthesis.

In order to obtain a process gas mixture having a reduced ammonia content vis-à-vis the crude HCN gas mixture, the ammonia contained in the crude HCN gas mixture is partially removed. This partial removal of ammonia is performed via an ammonia adjustment step. In said ammonia adjustment step, the ammonia from crude HCN gas is partially removed to an adjustable portion.

The ammonia adjustment is achieved by subjecting only part of the crude HCN gas to ammonia scrubbing and recombining the ammonia-free HCN gas and the remaining crude HCN gas. For ammonia scrubbing, the gas mixture is washed with sulfuric acid. In one specific embodiment, the gas mixture is washed with dilute sulfuric acid.

The terms "partial removal of ammonia", "ammonia depletion" and "ammonia adjustment" are used interchangeably in this text and have similar meaning. The term "ammonia-adjusted HCN gas mixture" will be used in the following for the gas mixture as obtained from crude HCN process gas by partial removal of ammonia. Specific embodiments of the ammonia adjustment step will be described in detail below.

The crude HCN process gas mixture, after production according to Andrussow, is typically at temperatures of >1000° C. and is therefore immediately cooled in order to prevent decomposition of the hydrogen cyanide. This cooling of the HCN-containing gas mixture prior to the ammonia adjustment step can be conducted, for example, by means of one or more heat exchangers connected in series. In this case, the energy can be withdrawn stepwise or continuously from the crude HCN gas mixture and optionally further used at another point in the process or externally. The temperature of the HCN-containing gas stream directly before ammonia adjustment may be from 0 to 800° C., from 10 to 500° C., or from 20 to 300° C.

The temperature maintained during the ammonia adjustment and/or ammonia scrubbing may be from 15° C. to 70° C., from 25° C. to 55° C., or from 30° C. to 50° C.

The temperature applied for contacting a gas mixture comprising HCN and ammonia with MMP may be from 0 to 300° C., from 0 to 100° C., or from 0 to 80° C.

Contacting the ammonia-adjusted HCN gas mixture with 3-methylmercaptopropionaldehyde (MMP) may be performed in different ways. For example, the gaseous mixture comprising (HCN) and ammonia may be absorbed by liquid MMP. The contacting of the ammonia-adjusted HCN gas mixture with liquid MMP may be carried out in an absorption tower or another apparatus suitable for the purpose, in which efficient mixing of gaseous and liquid constituents is possible, and in which relatively rapid conversion of MMP and HCN to MMP-CN can be achieved. Further possible embodiments include a stirred reactor, a loop reactor or a cascade of such reactors connected in series.

The ammonia-adjusted HCN gas mixture and the liquid MMP are preferably brought into contact with each other in countercurrent. In case an absorption tower is used, the gas mixture comprising HCN and ammonia is preferably introduced in the lower section of such an absorption tower, while the liquid MMP is introduced into the upper part of this tower.

After contacting the ammonia adjusted as mixture comprising hydrogen cyanide (HCN) and ammonia with 3-methylmercaptopropionaldehyde (MMP), a product mixture comprising MMP-CN and the corresponding amino derivatives 2-amino-4-(methylthio)butyronitrile (MMP-AN) and 2,2'-bis(2-(methylmercaptoethyl)iminodiacetonitrile (iminodinitrile) is obtained.

This product mixture comprising MMP-CN can be separated into a gaseous mixture and a liquid mixture. The gaseous mixture (offgas), comprising nitrogen, hydrogen and/or methane, is optionally further purified. It can be used as fuel gas to obtain energy or to obtain individual constituents, hydrogen for example.

The liquid mixture, comprising MMP-CN, can either be purified or used directly in subsequent steps as described below.

For logistic and process technology reasons, it may be advantageous or necessary not to convert a mixture comprising MMP-CN in further process steps, e.g. of the methionine synthesis, directly after its preparation, but rather time-delayed, after intermediate storage. It is important in this case that the intermediate product MMP-CN is stable over a relatively long period, i.e. can be stored without considerable decomposition of cyanohydrin.

The method according to the invention may therefore further comprise an additional process step, in which the product mixture comprising MMP-CN is stored at temperatures no higher than 60° C., preferably no higher than 40° C., particularly preferably no higher than 20° C. and a pH of 2 to 8, preferably 4 to 7, before this product mixture is further reacted.

The aforementioned ammonia adjustment step for partially removing ammonia from the crude HCN process gas mixture may be performed by using an ammonia scrubber equipped with a bypass stream.

Figure 1:
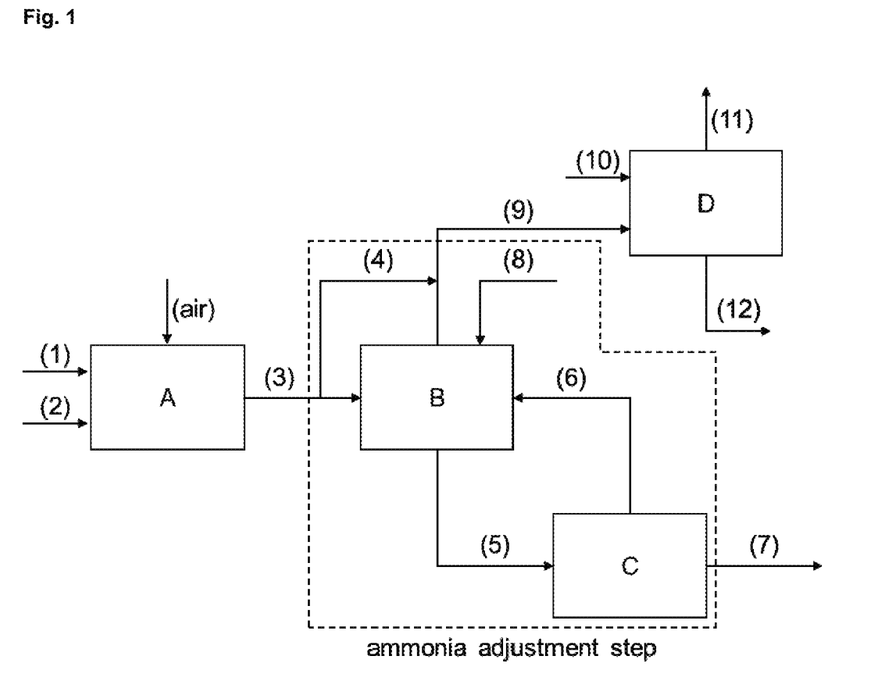
FIG. 1 depicts a plant system for the production of 2-hydroxy-4-(methylthio)butyronitrile (MMP-CN).

FIG. 1 depicts a plant system for the production of 2-hydroxy-4-(methylthio)butyronitrile (MMP-CN). The plant system comprises a HCN reactor (A), an ammonia scrubber (B), a HCN stripper (C) and a reactive absorber (D).

In reactor (A), HCN is prepared e.g. in accordance with the Andrussow process. The ammonia scrubber (B) is embedded in an ammonia adjustment unit (dotted lines) and may be equipped with a bypass stream (4) which enables the partial removal of process ammonia (ammonia adjustment). In the HCN stripper (C), the HCN dissolved in the crude ammonia sulfate solution is released in gaseous form. In reactive absorber (D), the gas mixture comprising HCN and ammonia obtained from a crude HCN gas mixture by partial removal of ammonia, i.e. the gas mixture obtained after the ammonia adjustment step, is reacted with MMP to give MMP-CN.

In an alternative embodiment of the present invention, the ammonia adjustment or partial removal of ammonia is performed by using an ammonia scrubber enabling a partial ammonia breakthrough.

Figure 2:
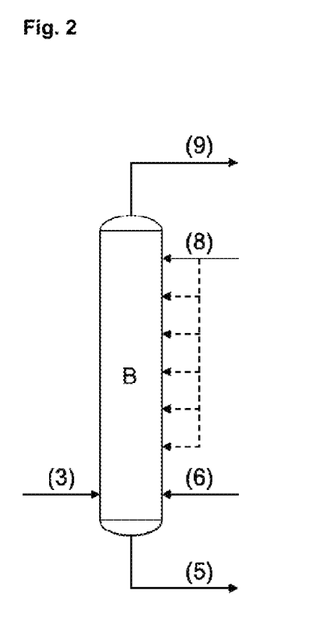
FIG. 2 shows the ammonia scrubber as in FIG. 1 with multiple options for the sulfuric acid feed position. Reference numbers/letters and explanations are identical to FIG. 1.

FIG. 2 shows two options for realization of a partial ammonia breakthrough through the ammonia scrubber (B).

For the first option the sulfuric acid concentration in the sulfuric acid feed stream (8) is reduced. Thereby, the reaction rate of absorbed ammonia to ammonium sulfate is limited and thus the absorption rate of ammonia. Ammonia will not be fully absorbed, but will partially stay in the gas phase and leave the ammonia scrubber at the top.

For the second option, the feed position of the sulfuric acid feed stream (8) is lowered. The lower the feed position, the more the mass transfer area in the ammonia scrubber is reduced. The reduction in mass transfer area leads to a limitation of absorption rate of ammonia into the liquid phase and thus ammonia will partially leave the ammonia scrubber at the top.

The crude HCN process gas mixture may be prepared according to the Andrussow process. In this oxidizing process, a gas mixture essentially comprising HCN, ammonia and water is prepared in an exothermic reaction from methane, ammonia and oxygen. Air is normally used as oxygen source. The product mixture after the HCN synthesis typically additionally comprises other gases such as nitrogen, argon, hydrogen, carbon monoxide, carbon dioxide and methane.

As an example, in one specific embodiment in which the Andrussow process serves as a source of the crude HCN gas mixture, the amount of ammonia in the gas mixture comprising HCN and ammonia is adjusted to a maximum amount of 60% (v/v) of the ammonia in the crude HCN gas mixture by bypassing a maximum amount of 60% (v/v) of the crude HCN gas mixture from the ammonia scrubber.

In the context of this specific embodiment, the expression "bypassing a defined amount of the crude HCN gas mixture from the ammonia scrubber" includes any method providing a secondary flow of the crude HCN gas mixture which does not get into contact with the ammonia scrubbing solution.

As an example, the ammonia scrubber equipped with a bypass stream as depicted in FIG. 1 may be used for bypassing the above-defined amount of the crude HCN gas mixture from the ammonia scrubber Alternatively, ammonia adjustment may be performed by using an ammonia scrubber enabling a partial ammonia breakthrough, as depicted in FIG. 2.

Advantageously, the amount of ammonia in the gas mixture comprising HCN and ammonia is adjusted to a maximum amount of 40% (v/v) of the ammonia in the crude HCN gas mixture by bypassing a maximum amount of 40% (v/v) of the crude HCN has mixture from the ammonia scrubber when Andrussow technology is used for the preparation of HCN.

By the aforementioned adjustment to a maximum amount of 60% (v/v), or of 40% (v/v), respectively, of the ammonia in the crude HCN gas mixture obtained via Andrussow, the formation of biphasic mixtures in the storage tanks and/or in the reactive absorber can be efficiently circumvented.

In addition, the subject invention provides a specific product mixture comprising MMP-CN, as obtainable by contacting the above-described ammonia-adjusted gas mixture comprising HCN and ammonia with MMP. Said product mixture comprises, besides the MMP-CN, its corresponding amino derivatives 2-amino-4-(methylthio) butyronitrile (MMP-AN) and 2,2'-bis(2-(methylmercaptoethyl)iminodiacetonitrile (iminodinitrile).

The main components of the Andrussow HCN process gas composition obtained by the aforementioned ammonia adjustment ratios are listed in Table 2 for typical HCN raw gas compositions of this HCN synthesis processes.

TABLE 2

| Adjustment ratios for crude Andrussow HCN gas | | | |
| --- | --- | --- | --- |
| Adjustment Ratio % | HCN mol HCN/ mol HCN | $H_2O$ mol $H_2O$/ mol HCN | $NH_3$ mol $NH_3$/ mol HCN |
| 5 | 1.00 | 0.78 | 0.01 |
| 10 | 1.00 | 0.90 | 0.03 |
| 80 | 1.00 | 2.54 | 0.23 |
| 90 | 1.00 | 2.78 | 0.26 |

The present invention further provides a method for producing methionine or salts or derivatives thereof from MMP-CN, wherein the 2-hydroxy-4-(methylthio)butyronitrile (MMP-CN) is obtained by any one of the aforementioned methods.

Said method for producing methionine optionally comprises a step of reacting 2-hydroxy-4-(methylthio)butyronitrile (MMP-CN) or a crude product mixture comprising MMP-CN with ammonia and/or ammonium salts and carbon dioxide and/or carbonic acid salts to give 5-(2-methylmercaptoethyl)hydantoin.

For hydantoin synthesis, 2-hydroxy-4-(methylthio)butyronitrile (MMP-CN) can be used either in purified form or as crude product mixture as obtained directly from contacting the ammonia-adjusted gas mixture with MMP. As indicated above, said product mixture comprises, besides the MMP-CN, its corresponding amino derivatives 2-amino-4-(methylthio)butyronitrile (MMP-AN) and 2,2'-bis(2-(methylmercaptoethyl)iminodiacetonitrile (iminodinitrile).

The reaction to give the hydantoin can be carried out, for example, in a stirred pressure reactor at elevated temperature. The ammonia and carbon dioxide required for this reaction may be introduced into this process step as corresponding gases, singly or as a mixture, optionally with water, or at least partially as the corresponding ammonium carbonate and/or ammonium hydrogen carbonate salts or aqueous solutions thereof. In aqueous solutions, ammonia, carbon dioxide, carbonate ions, hydrogen carbonate ions and ammonium ions are in equilibrium with one another.

It was shown that not only MMP-CN but also the main by-products MMP-AN mentioned above and, even the relatively stable iminodinitrile, can be successfully reacted to give the hydantoin.

The thus-obtained 5-(2-methylmercaptoethyl)hydantoin may then be reacted under basic conditions with formation of carbon dioxide and ammonia to give at least one methionine salt. Said methionine salt may be further reacted with an acid to give methionine.

The bases used may be, for example, oxides, hydroxides, carbonates or other salts of the alkali metals or alkaline earth metals, the rare earth metals or ammonium salts and also mixtures of these bases. Particular preference is given to using carbonates or hydrogen carbonates of the alkali metals or ammonium, particularly preferably potassium, sodium or ammonium carbonate or mixtures thereof.

The method according to the invention for preparing methionine or a salt of methionine may be carried out batchwise or continuously, preferably continuously.

In addition to the formation of methionine or methionine salts, the product mixture comprising MMP-CN obtained according to the method of the present invention may also be reacted in further process steps, according to US 20110295006 A1 for example, to give 3,6-bis(2'-methylmercaptoethyl)-2,5-diketopiperazine (DKP) or, according to DE 2261926 A1, to give the dipeptide of methionine, methionylmethionine (Met-Met).

Finally, the present invention pertains to a plant system for the production of 2-hydroxy-4-(methylthio)butyronitrile (MMP-CN).

The plant system is depicted in FIG. 1 and comprises a HCN reactor vessel (A) and a reactive absorber (D) for reacting hydrogen cyanide with 3-methylmercaptopropionaldehyde (MMP). The Andrussow hydrogen cyanide reactor (A) is interconnected with the reactive absorber via an ammonia adjustment unit comprising an ammonia scrubber (B) having a bypass stream/bypassing gas line (4).

The ammonia adjustment unit is depicted in FIG. 1 as dotted lines.

The ammonia adjustment unit may further comprise a HCN stripper (C) with stripped HCN recycle stream (6) and crude ammonium sulfate stream (5). The ammonium sulfate product mixture exits the ammonia adjustment unit via stream (7). The ammonia scrubber is fed with sulfuric acid via feed stream (8). The ammonia-adjusted gas stream (9) connects the ammonia adjustment unit with the reactive absorber (D).

The MMP feed stream is shown as (10), the offgas stream is shown as (11) and the MMP-CN product mixture is shown as (12).

In the following, the invention is illustrated by non-limiting examples and exemplifying embodiments.

EXAMPLES

Overview
  Example 1 (comparative). Production of MMP-cyanohydrin from ammonia containing hydrocyanic acid without adjustment step
  Example 2. Miscibility of ammonia containing MMP-cyanohydrin solution with water
  Example 3. Adjustment of the $NH_3$ to HCN ratio and the water content for the Andrussow process to avoid the separation of two liquid phases
  Example 4. Adjustment of the $NH_3$ to HCN ratio and the water content Example 5. Exemplary composition of a hydrocyanic acid gas stream after the adjustment step
  Example 6. Exemplary synthesis of methionine via MMP-cyanohydrin produced with a breakthrough adjustment step
Methods Used
Calculation of Ammonia Adjustment Unit The product steams after the ammonia adjustment unit (FIG. 1, streams 9 and 7) comprising a sulfuric acid washer (B) to remove ammonia by forming ammonium sulfate, a stripper (C) to remove excess hydrogen cyanide from the ammonium sulfate solution and a bypass stream (4) were calculated by mass and heat transfer and reaction rates. Crude hydrogen cyanide reaction gas (3) and fresh sulfuric acid (98 wt %) (8) are fed to the washer (B). The ammonium sulfate solution (5) is fed to the stripper (C) and excess HCN is removed by in-situ evaporated steam. The ammonium sulfate product stream (7) is set to have less than 0.1 wt ppm of hydrogen cyanide, the adjusted HCN gas stream (9) is the target stream that is fed to a subsequent MMP-cyanohydrin formation step (D).

Well established physical property data for the applied chemical system have been applied using a standard process simulator (Aspen Plus by aspentech).

Determination of Water Content by Karl Fischer Titration

The $H_2O$ content in MMP-CN was determined by titration using biamperometric indication of the end point (Karl Fischer titration).

For this purpose, 20-30 mL of titration medium (e.g. Hydranal Solvent 5 from Fluka), were initially charged in the titration vessel and titrated to dryness with titrant (e.g. Hydranal Titrant 5 from Fluka). An amount of sample of ca. 500 mg was added to the titrated reservoir (plastic disposable syringe) and titrated with the titrant to the end point. The precise sample weight was determined by differential weighing.

This is a standard method known to experts in the field (see e.g. P. A. Bruttel, R. Schlink: *Wasserbestimmung durch Karl-Fischer-Titration* [*Water determination by Karl Fischer titration*] Metrohm AG).

High Performance Liquid Chromatography (HPLC)

The majority of the chromatographic investigations (MMP-cyanohydrin, MMP, MMP-aminonitrile, methionine, methionine amide, hydantoin, hydantoin amide, Met-Met, methionine diketopiperazine) were carried out by HPLC from JASCO on an RP-18 column (250×4.6 mm; 5 μm) with subsequent UV detection at 210 nm. A phosphoric acid-acetonitrile-water mixture (3.3 g $H_3PO_4$, 6.8 g acetonitrile, 89.9 g $H_2O$) served as eluent. At a flow rate of 1 mL/min, 10 μL of the respective sample solution (50 mg of sample in 25 mL of $H_2O$) were injected. Calibration was effected in advance by the injection of suitable calibration solution and evaluated by peak area comparison by means of the external standard method. This is a standard method known to experts in the field.

The iminodinitrile was analyzed on the HPLC system specified above with identical column, flow rate and detection. In this case, a mixture of methanol and water (each 50% by weight) served as eluent. 10 μL of the respective sample solution (250 mg of sample in 25 mL of eluent) were injected.

Example 1

Production of MMP-Cyanohydrin from Ammonia Containing Hydrocyanic Acid without Ammonia Adjustment Unit 188 g of 3-methylthiopropionaldehyde (methylmercaptopropionaldehyde, MMP) (94.0 wt %, 1.00 equiv.) from industrial production were metered in at a rate of 6 g/min at the top of a bubble-tray column temperature-controlled at 55° C. (5 trays, double jacketed) equipped with a reflux condenser. At the bottom of the column an Andrussow gas mixture containing hydrocyanic acid (47.0 g, 1.02 equiv. based on MMP, 90 g/h), ammonia (7.99 g, 0.28 equiv. based on MMP, 15.3 g/h), steam (80 g, 156 g/h) and nitrogen (230 NL, 450 NL/h) ($NH_3$:HCN=0.27 mol/mol) was added by countercurrent principle. The product was collected in a flask fixed to the bottom of the column and analyzed after completion of the MMP addition (ca. 30 min). A clear, colourless biphasic product was obtained: one part aqueous layer at the top and five parts organic layer at the bottom. HPLC analysis revealed a total content of 145 g of MMP-cyanohydrin (MMP-CN, 65.1% based on MMP used), 33.8 g of MMP-aminonitrile (MMP-AN, 15.3% based on MMP used) and 30.6 g of iminodinitrile (14.8% based on MMP used). MMP-CN, MMP-AN and iminodinitrile are further referred to as ammonia-containing MMP-CN equivalents or MMP-cyanohydrin equivalents.

Example 2

Miscibility of Ammonia Containing MMP-Cyanohydrin Equivalents with Water

An ammonia adjustment unit will alter both the ammonia and water content in the HCN gas. In order to determine the limit of water allowed to receive the resultant ammonia-containing MMP-CN equivalents as a single phase, miscibility experiments of water and MMP-CN with varying ammonia content were conducted.

In a three-necked flask cooled in an ice bath, equipped with jacketed coil condenser and thermometer, gaseous ammonia was slowly passed through a mechanically stirred sample of 93 g of MMP-cyanohydrin (96% by weight, 1.0 equiv.) until differential weighing confirmed addition of 1.16 g (0.1 equiv.) of ammonia ($NH_3$:HCN=0.10 mol/mol). The resultant solution was allowed to warm to room temperature and stirred for three days. HPLC analysis confirmed complete conversion of the ammonia to iminodinitrile; MMP-AN was not present. 10 g of the mixture were cooled to 10° C. in a double-jacketed flask and stirred vigorously. Water was slowly added dropwise until phase separation occurred (i.e. turbidity, droplets or second layer). A total of 2.16 g of water was added, corresponding to a max. solubility of 17.8 wt % of water in ammonia containing MMP-CN equivalents prepared from $NH_3$:HCN=0.1 mol/mol. The experiment was repeated at 30° C. as well as with varying ratios of $NH_3$:HCN. The results are listed in table 3.

TABLE 3

Maximum miscibility of ammonia containing MMP-cyanohydrin equivalents with water depending on ammonia content and temperature.

| Molar ratio of $NH_3$:HCN | T = 10° C. | T = 30° C. |
|---|---|---|
| | max. solubility of water in wt % | |
| 0.05 | 19.8 | 22.4 |
| 0.075 | 15.6 | 20.0 |
| 0.1 | 17.8 | 22.0 |
| 0.1 | 16.4 | 20.9 |
| 0.15 | not measured | 17.0 |
| 0.2 | not measured | 15.8 |

Figure 3:
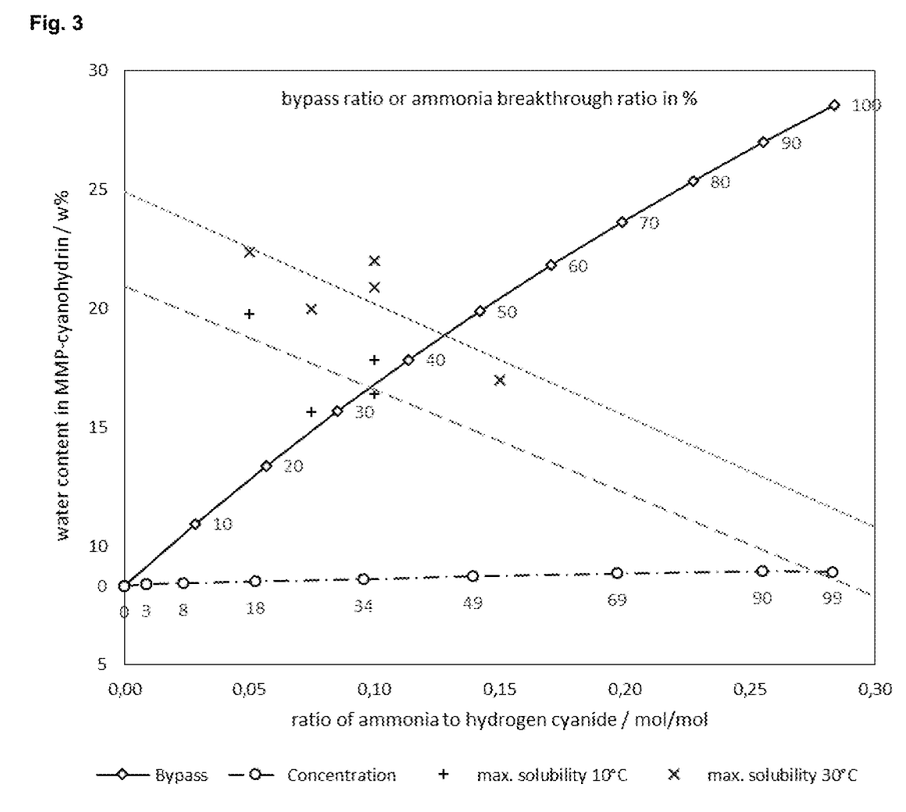
FIG. 3: Experimental results and linear approximation of the maximum miscible water content in MMP-cyanohydrin as a function of the molar NH$_3$ to HCN ratio at 10 and 30° C.

The experimental results and linear approximation of the maximum miscible water content in MMP-cyanohydrin at 10 and 30° C. are shown in FIG. 3 as a function of the molar $NH_3$ to HCN ratio.

Example 3

Adjustment of the $NH_3$ to HCN Ratio and the Water Content for the Andrussow Process to Avoid the Separation of Two Liquid Phases A standard crude hydrogen cyanide reaction gas stream (3) produced by an Andrussow reaction step comprising 6.5 mol % hydrogen cyanide, 1.8 mol % ammonia and 19.6 mol % water is fed to the ammonia adjustment unit (IHS Chemical PEP Review 2015-07 "Hydrogen Cyanide by the Andrussow and BMA Process"). The ammonia and water contents after the adjustment step by bypassing (4) the sulfuric acid washer (B) are calculated for bypass ratios from 0 to 100%. The adjusted hydrogen cyanide stream (9) used in an MMP-cyanohydrin reaction step (D) with pure MMP (10) as reacting agent leads to a corresponding water content in the MMP-cyanohydrin equivalents solution (12) as shown in FIG. 3 (indicated as "Bypass"). The data labels inside the diagram represent the bypass ratio (percentage of reaction gas stream that is led via the bypass) or the ammonia breakthrough ratio (percentage of ammonia in the reaction gas stream that breaks through the column into the product gas stream (9)). For this particular crude hydrogen cyanide reaction gas composition a maximum bypass ratio of 35% (45%) is feasible without the risk of two separated liquid phases in the MMP-cyanohydrin reaction step or subsequent storage for an operating temperature of 10° C. (30° C.). The higher the operating temperature, the higher the maximum bypass ratio without the risk of phase separation will be.

The alternative adjustment of the same hydrogen cyanide reaction gas stream is by ammonia breakthrough through the sulfuric acid washer by reducing the feed flow rate (8) of sulfuric acid to the washer (B). FIG. 3 shows the water and ammonia contents in the corresponding MMP-cyanohydrin equivalents solution starting from a 2% stoichiometric excess of sulfuric acid (indicated as "Concentration"). For this particular crude hydrogen cyanide reaction gas composition by reducing the sulfuric acid feed flow rate a maximum breakthrough of ammonia of 97% (100%) is feasible without the risk of two separated liquid phases in the MMP-cyanohydrin reaction step or subsequent storage for an operating temperature of 10° C. (30° C.).

Example 4

Adjustment of the $NH_3$ to HCN Ratio and the Water Content

Figure 4:
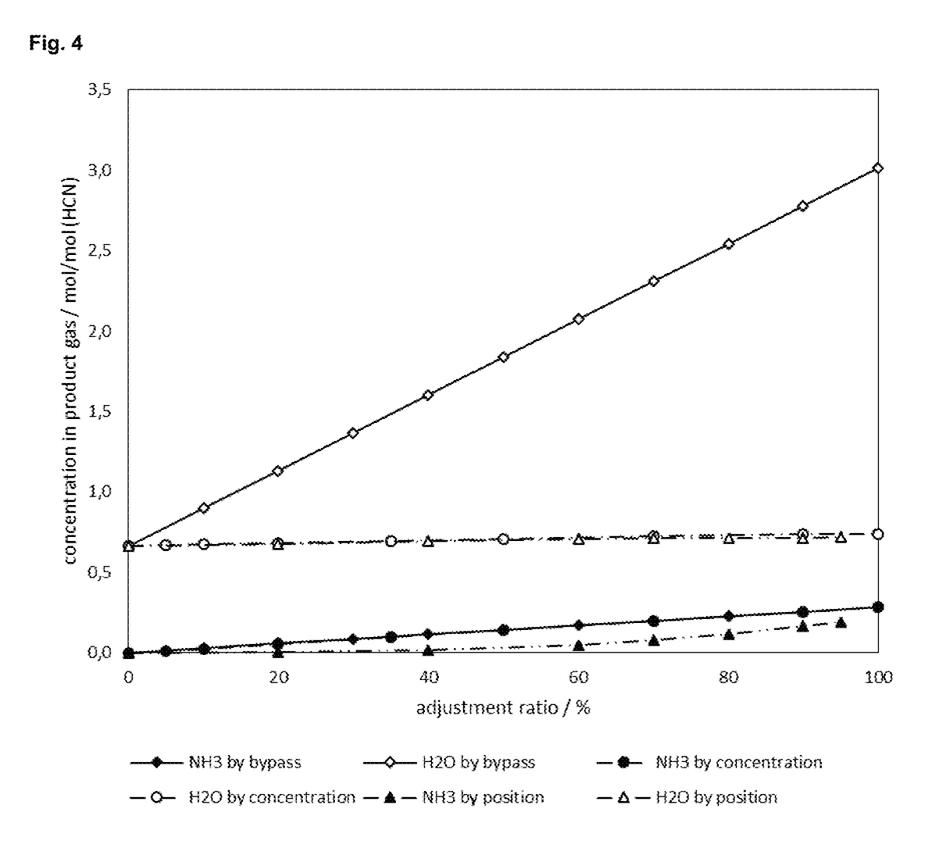
FIG. 4: Calculated concentration of water and ammonia in the hydrogen cyanide gas stream after the adjustment step (9) for standard crude hydrogen cyanide reaction gas stream from an Andrussow reaction step as a function of the ratio of ammonia adjustment.

The calculated concentrations of water and ammonia in the hydrogen cyanide gas stream after the adjustment step (9) for the Andrussow crude hydrogen cyanide reaction gas stream as mentioned in Example 3 are shown in FIG. 4 as a function of the ratio of adjustment. The ratio of adjustment represents either the percentage of reaction gas that is led via the bypass ("bypass"), the percentage of reduction of sulfuric acid concentration ("concentration") or the percentage of lowering the feed position for the sulfuric acid stream ("position"). In FIG. 2 the lowering of the feed position for the sulfuric acid (8) to the ammonia washer (B) is illustrated. The lower the feed position, the less area for mass transfer is available and the more ammonia is not absorbed but breaks through the washer.

For adjustment by bypass the water and ammonia concentration in the gas stream after the adjustment step is almost linear to the ratio of adjustment. For adjustment by breakthrough by reduction of sulfuric acid concentration, the water concentration stays almost constant and the ammonia concentration is almost linear to the ratio of adjustment. For adjustment by breakthrough by lowering the feed position for the sulfuric acid stream, the water and ammonia concentration lags the increase of the adjustment ratio. 100% adjustment by breakthrough by lowering the feed position corresponds to a complete stop of sulfuric acid feed flow rate to the washer.

Both adjustment options, bypass and breakthrough, allow a full control of the ammonia concentration in the gas stream after the adjustment step and the production rate of ammonium sulfate.

Example 5

Exemplary Composition of a Hydrocyanic Acid Gas Stream after the Ammonia Adjustment Unit The full composition of the HCN gas stream (9) after the adjustment step as calculated in Example 3 for an Andrussow reaction step is shown in Table 4 a for selected adjustment ratios.

TABLE 4

Exemplary compositions and ammonium sulfate production rates for a hydrogen cyanide stream produced by an Andrussow reaction step adjusted by bypassing the sulfuric acid wash.

| | 0% bypass ratio | 30% bypass ratio | 100% bypass ratio |
|---|---|---|---|
| Composition of product stream (9) in mol % | | | |
| methane | 0.3 | 0.2 | 0.2 |
| ethane | 0.3 | 0.3 | 0.3 |
| ammonia | 0.0 | 0.7 | 1.8 |
| water | 1.2 | 7.6 | 19.6 |

TABLE 4-continued

Exemplary compositions and ammonium sulfate production rates for a hydrogen cyanide stream produced by an Andrussow reaction step adjusted by bypassing the sulfuric acid wash.

| | 0% bypass ratio | 30% bypass ratio | 100% bypass ratio |
|---|---|---|---|
| hydrogen cyanide | 8.1 | 7.6 | 6.5 |
| nitrogen | 71.9 | 66.8 | 57.2 |
| oxygen | 4.2 | 3.9 | 3.4 |
| carbon monoxide | 3.7 | 3.5 | 3.0 |
| carbon dioxide | 0.4 | 0.4 | 0.3 |
| hydrogen | 9.8 | 9.1 | 7.8 |
| propane | 0.0 | 0.0 | 0.0 |
| butane | 0.0 | 0.0 | 0.0 |
| Ammonium sulfate production rate in kg (ammonium sulfate)/to (hydrogen cyanide) | | | |
| ammonium sulfate | 688 | 481 | 0 |

Example 6

Exemplary Synthesis of Methionine Via MMP-Cyanohydrin Produced with a Breakthrough Ammonia Adjustment Unit In a 300 mL autoclave beaker equipped with a stirrer bar, distilled water (37 g), ammonium carbonate (13.9 g) and ammonium hydrogen carbonate (20.2 g) were added to 34.7 g of MMP-cyanohydrin prepared from hydrocyanic acid with adjusted ammonia-content ($NH_3$:HCN=0.087 mol/mol, cf. table 4 with 30% bypass), consisting of 68.4 wt % MMP-CN and 16.5 wt % iminodinitrile. The reaction vessel was transferred to a high-pressure laboratory autoclave from ROTH, equipped with manometer, heater, temperature sensor, inlet tube and pressure release. The autoclave was tightly sealed, heated with stirring to 105° C. over a period of 15 min and then maintained at this temperature for a further 30 min. At the end of the reaction period, the autoclave was cooled to 70° C. in a water bath and the resulting pressure (ca. 15 bar) was vented. Aqueous KOH solution (31.1 g of KOH in 42.5 g of H2O) was then metered in via the inlet tube over a period of 10 min. After the addition was complete, the autoclave was heated with stirring to 180° C. over a period of 25 min and then maintained at this temperature for a further 30 min. During the course of the reaction, the pressure was vented to 5 bar around every 5 min, but at least in the case of 10 bar being exceeded. At the end of the reaction period, the autoclave was cooled to room temperature under running cooling water and depressurized to standard pressure. HPLC analysis of the reaction product confirmed formation of 75.4% of methionine and 5.1% of Met-Met.

The invention claimed is:
1. A method for producing 2-hydroxy-4-(methylthio) butyronitrile (MMP-CN), comprising:
 a) preparing a crude HCN process gas mixture by Andrussow HCN synthesis from methane, ammonia and oxygen;
 b) preparing an HCN process gas mixture by adjusting the amount of ammonia in the crude HCN process gas mixture to between 20% (v/v) and 60% (v/v) of the amount present before adjustment; and
 c) contacting the HCN process gas mixture with 3-methyl-mercaptopropionaldehyde (MMP).
2. The method of claim 1, wherein the ammonia adjustment is performed using an ammonia scrubber equipped with a bypass stream.

3. The method of claim 1, wherein the ammonia adjustment is performed using an ammonia scrubber enabling a partial ammonia breakthrough.

4. The method of claim 1, wherein the ammonia is adjusted in step b) to about 40% (v/v) of the ammonia in the crude HCN process gas mixture.

5. The method of claim 4, wherein adjustment is made using an ammonia scrubber.

6. A method for producing methionine, salts of methionine or derivatives of methionine from HCN, the method comprising:
   a) preparing a crude HCN process gas mixture by Andrussow HCN synthesis from methane, ammonia and oxygen;
   b) preparing an HCN process gas mixture by adjusting the amount of ammonia in the crude HCN process gas mixture to between 20% (v/v) and 60% (v/v) of the amount present before adjustment; and
   c) contacting the HCN process gas mixture with 3-methyl-mercaptopropionaldehyde (MMP) to produce 2-hydroxy-4-(methylthio)-butyronitrile (MMP-CN), or a crude product mixture comprising MMP-CN; and
   d) further reacting the MMP-CN or crude product mixture comprising MMP-CN of step c) to produce said methionine, salts of methionine or derivatives of methionine.

7. The method of claim 6, wherein step d) comprises reacting the 2-hydroxy-4-(methylthio) butyronitrile (MMP-CN) or the crude product mixture comprising MMP-CN, with ammonia and/or ammonium salts and carbon dioxide and/or carbonic acid salts to give 5-(2-methylmercaptoethyl) hydantoin.

8. The method of claim 7, wherein step d) further comprises reacting the 5-(2-methylmercapto-ethyl) hydantoin under basic conditions with formation of carbon dioxide and ammonia to give at least one methionine salt.

9. The method of claim 8, wherein step d) further comprises reacting reacting the methionine salt with an acid to give methionine.

* * * * *